United States Patent
Johnson

(10) Patent No.: US 7,910,371 B2
(45) Date of Patent: *Mar. 22, 2011

(54) METHOD OF MONITORING TREATING AGENT RESIDUALS IN WATER TREATMENT PROCESSES

(75) Inventor: Brian S. Johnson, Warrenville, IL (US)

(73) Assignee: Nalco Company, Naperville, IL (US)

( * ) Notice: Subject to any disclaimer, the term of this patent is extended or adjusted under 35 U.S.C. 154(b) by 991 days.

This patent is subject to a terminal disclaimer.

(21) Appl. No.: 11/038,718

(22) Filed: Jan. 20, 2005

(65) Prior Publication Data

US 2006/0160226 A1    Jul. 20, 2006

(51) Int. Cl.
*G01N 33/52* (2006.01)
(52) U.S. Cl. ............. 436/55; 436/56; 436/172; 210/709
(58) Field of Classification Search .................... 436/55, 436/56, 172; 422/62; 210/709
See application file for complete search history.

(56) References Cited

U.S. PATENT DOCUMENTS

| | | | |
|---|---|---|---|
| 3,939,070 A * | 2/1976 | Roth | ............................. 210/636 |
| 5,389,548 A | 2/1995 | Hoots et al. | |
| 5,413,719 A | 5/1995 | Sivakumar et al. | |
| 5,645,799 A | 7/1997 | Shah et al. | |
| 5,705,394 A * | 1/1998 | Ananthasubramanian et al. | .................................... 436/55 |
| 6,730,227 B2 | 5/2004 | Zeiher et al. | |
| 6,821,428 B1 | 11/2004 | Zeiher et al. | |
| 6,838,001 B2 | 1/2005 | Zeiher et al. | |
| 6,838,002 B2 | 1/2005 | Zeiher et al. | |
| 7,179,384 B2 * | 2/2007 | Moriarty et al. | ............. 210/698 |

FOREIGN PATENT DOCUMENTS

WO    WO 99/51817    10/1999

OTHER PUBLICATIONS http://www.thefreedictionary.com/—"tracer" and "taggant".*

* cited by examiner

*Primary Examiner* — Jan M Ludlow
(74) *Attorney, Agent, or Firm* — Joshua D. Bishop; Michael B. Martin

(57) ABSTRACT

A method of monitoring residual treating agent in treated water wherein fluorescent tracers are used to determine the concentration of treating agent in the water at two different treating agent dosages and the difference in the measured concentrations of the fluorescent tracer at the respective doses are correlated with the residual concentration of the treating agent. The fluorescence response at the different treating agent dosages is used to determine whether the system is overdosed or underdosed on a continuous basis and to control treating agent dose accordingly.

23 Claims, No Drawings

METHOD OF MONITORING TREATING AGENT RESIDUALS IN WATER TREATMENT PROCESSES

TECHNICAL FIELD

This invention relates to water treatment. More particularly, this invention is a method of using fluorescent tracers to monitor the residual concentration of treating agents in treated water as a function of tracer fluorescence at two different treating agent dosages.

BACKGROUND OF THE INVENTION

Water, in the course of its use in industrial, municipal and agricultural applications may be treated with an astounding array of treatment agents including, for example, chemicals that enhance solid-liquid separation, membrane separation process performance enhancers, antiscalants and anticorrosives that retard or prevent corrosion or scale formation and deposition on surfaces in contact with the treated water, antifoulants that retard or prevent membrane fouling, biodispersants, microbial-growth inhibiting agents such as biocides and cleaning chemicals that remove deposits from surfaces that contact the treated water.

Control of treating agent dosage is of paramount importance in virtually all water treatment processes. Obviously, a minimum effective amount of treating agent must be maintained in the water for the treatment to have its desired effect. Conversely, overdosing the treating agent would be at best uneconomical and at worst could result in damage to the process or the processing equipment, particularly in the case of processes involving the use of membranes as described herein. Accordingly, there is an ongoing need for the development of improved methods of monitoring and controlling the concentration of water treatment agents in process water.

SUMMARY OF THE INVENTION

This invention is a method of monitoring residual treating agent in water treatment process water comprising
i) adding a first dose of a treating agent traced or tagged with a fluorescent tracer to a first sample of the process water,
ii) measuring the concentration of the fluorescent tracer in the first sample of the process water,
iii) adding a second dose of the treating agent traced or tagged with the fluorescent tracer to a second sample of the process water;
iv) measuring the concentration of the fluorescent tracer in the second sample of the process water; and
v) correlating the change in the measured concentration of the fluorescent tracer at the first and second treating agent doses to the residual concentration of the treating agent.

DETAILED DESCRIPTION OF THE INVENTION

This invention allows for treating agent residual monitoring by utilizing fluorescent molecules. These molecules are selected such that they interact or associate with the treating agent. It is this interaction that partitions the fluorescent chromophore population between different microenvironments. This partitioning changes (i.e. reduces) the fluorescent properties such that the fluorescence is not as detectable. The two microenvironments are free chromophore (i.e. dissolved in water) and chromophore associated with treating agent (i.e. 'bound' chromophore). Therefore, when the treated water contains treating agent residuals, the fluorescence is lower than expected since the 'bound' chromophores are not detected. This difference between expected and actual fluorescence is used to quantitatively estimate the treating agent residuals. By using fluorescence response and treating agent dose at two points, the treating agent residuals can be estimated from a calibration curve.

In an embodiment, the treating agent residuals can be estimated as a function of the difference between fluorescent molecules added to the water and fluorescent molecules detected in the water according to metric I.

$$\frac{(x_1 F_2 - x_2 F_1)}{(F_2 - F_1)} \qquad \text{I}$$

where $x_1$ and $x_2$ are the first and second product dose and $F_1$ and $F_2$ are the first and second fluorescence measurements, in arbitrary units. In an embodiment, the product dose is in ppm.

In an embodiment, the treating agent residuals can be estimated as a function of the difference between the quenching expected and the quenching detected according to metric II.

$$\frac{(x_1/F_2 - x_2/F_1)}{(1/F_2 - 1/F_1)} \qquad \text{II}$$

where $x_1$, $x_2$, $F_1$ and $F_2$ are defined above. Fluorescence can be in arbitrary units, but can also be expressed as ppb of tracer molecule.

For purposes of this invention, overall quenching means any process or processes that change the measured fluorescence such that the Stem-Volmer plot as described below is essentially linear. Put another way, "quenching" exists when the Stem-Volmer plot is linear.

In an embodiment, the residual concentration of the treating agent is correlated with treating agent dosage.

In an embodiment, the residual concentration of the treating agent is used to determine an upper and lower limit of treating dosage.

In an embodiment, the treating agent dosage is automatically maintained between the upper and lower limit.

In an embodiment optimal treating agent dosage is calculated using the inverse derivative of fluorescence response with respect to treating agent dose and empirically correlating to any water quality parameter reflective of system performance. Suitable water quality parameters include, but are not limited to turbidity, silt density index (SDI), particle counts, and the like. In an embodiment, this correlation is accomplished using standard jar test methods to measure fluorescence and a water quality parameter such as turbidity and then calculating the inverse derivative of fluorescence response with respect to treating agent dose. Then at the acceptable water quality parameter dose point, the derivative of the inverse fluorescence is the initial set point. Once implemented in full-scale, the set point will be fine-tuned for the optimal full-scale water process.

Inverse fluorescence can be related to quenching via Stem-Volmer plots. The Stem-Volmer relationship is: $1/I_f = (1+K_d[Q])/I_O$ where: $K_d$=Quenching Rate Constant, [Q]=Quencher(s) Concentration, $I_O$=Fluorescence w/o Quenching, $I_f$=Measured Fluorescence. As noted above, for purposes of this invention, quenching is defined as occurring when the Stem-Volmer plot is essentially linear.

Since $I_o$ is proportional to ppm of product added (=k*ppm), then $1/I_f = (1/k + K_d[Q]/k)*(1/ppm)+0$. Here 'k' is a product factor that describes the concentration of the fluorescent molecule (i.e. the tracer) in the product being dosed (i.e. the treating agent). Therefore, if fluorescence quenching is occurring, a plot of $1/I_f$ vs. $1/ppm$ is linear with a slope equal to $(1/k+K_d[Q])/k)$ and a Y-intercept of zero.

In an embodiment, the set point of the derivative of the inverse derivative of fluorescence response with respect to the treating agent dosage is used to automatically control treating agent dosage.

In an embodiment, an algorithm controls dosage iteration and calculates the slope and residual function as defined above. Dosage iteration refers to a method of making a small adjustment in dosage, allowing the system to equilibrate, then measuring some response.

More particularly, at a particular treating agent dosage (dose$_1$), the treated water's fluorescence ($F_1$) is measured. The treating agent dosage is then incremented to slightly different dose (dose$_2$) and the system is allowed to equilibrate. At this new dose, the fluorescence ($F_2$) is measured. In an embodiment, the time required for the system to equilibrate is the retention time of the system, i.e. the time needed for the fluorescence to adjust to a change in treating agent dosage. Equilibration time for filtration systems is typically about five to about ten minutes but can be longer depending on the particular system.

At this point the slope of the inverse fluorescence vs. dosage curve is calculated with the algebraic relationship: slope= $(1/F_1-1/F_2)/(dose_1-dose_2)$. This slope is compared to a setpoint determined as described above and if it is greater than the setpoint, dosage is incrementally reduced, if it is less, the dose is incrementally increased. This is what we term slope control. Then the measured fluorescence and dose information is used to calculate the ideal slope and this is the initial setpoint. Once the full-scale system is activated, the setpoint is fine-tuned for optimal system performance.

Polymer residuals are estimated by the fluorescence function using metrix I or II as described above and if the residuals are too high, the dosage is automatically reduced. In an embodiment, the residuals fluorescence function is used to monitor the system to ensure excessive residuals are not being fed to the treatment system. In another embodiment, the slope is used to automate the treating agent feed. Thus, the algorithm serves to maintain dosage control and insure that the treating agent residuals do not exceed an application specific set point.

For example, in reverse osmosis (RO) pretreatment systems, using iterative control allows for dosage adjustment for changing influent waters, which is different from a fluorescence set point, which is valid only for a set influent. This technology's main advantage is the ability to monitor treating agent residuals and thus allow for the use of treating agents (a.k.a.—polyelectrolytes) for RO pretreatment to reduce RO influent's silt density index (SDI) and minimize cleaning cost, labor and lost water production.

In an embodiment, the treating agent is traced with one or more fluorescent tracers. These fluorescent tracers may or may not be appreciably or significantly affected by any other chemistry in the water treatment process, or by the other system parameters such as pH, temperature, ionic strength, redox potential, microbiological activity or biocide concentration. As long as the chemistry in the water treatment process does not significantly change during the retention time (usually about ten minutes), the control algorithm automatically accounts for significant changes in fluorescence.

The fluorescent tracers must be transportable with the water treatment process water and thus are substantially, if not wholly, water-soluble therein at the use concentration, under the temperature and pressure conditions specific and unique to the water treatment process.

Representative fluorescent tracers include, but are not limited to 3,6-acridinediamine, N,N,N',N'-tetramethyl-, monohydrochloride, also known as Acridine Orange (CAS Registry No. 65-61-2), 2-anthracenesulfonic acid sodium salt (CAS Registry No. 16106-40-4), 1,5-anthracenedisulfonic acid (CAS Registry No. 61736-91-2) and salts thereof, 2,6-anthracenedisulfonic acid (CAS Registry No. 61736-95-6) and salts thereof, 1,8-anthracenedisulfonic acid (CAS Registry No. 61736-92-3) and salts thereof, anthra[9,1,2-cde]benzo[rst]pentaphene-5,10-diol, 16,17-dimethoxy-, bis(hydrogen sulfate), disodium salt, also known as Anthrasol Green IBA (CAS Registry No. 2538-84-3, aka Solubilized Vat Dye), bathophenanthrolinedisulfonic acid disodium salt (CAS Registry No. 52746-49-3), amino 2,5-benzene disulfonic acid (CAS Registry No. 41184-20-7), 2-(4-aminophenyl)-6-methylbenzothiazole (CAS Registry No. 92-36-4), 1H-benz[de]isoquinoline-5-sulfonic acid, 6-amino-2,3-dihydro-2-(4-methylphenyl)-1,3-dioxo-, monosodium salt, also known as Brilliant Acid Yellow 8G (CAS Registry No. 2391-30-2, aka Lissamine Yellow FF, Acid Yellow 7), phenoxazin-5-ium, 1-(aminocarbonyl)-7-(diethylamino)-3,4-dihydroxy-, chloride, also known as Celestine Blue (CAS Registry No. 1562-90-9), benzo[a]phenoxazin-7-ium, 5,9-diamino-, acetate, also known as cresyl violet acetate (CAS Registry No. 10510-54-0), 4-dibenzofuransulfonic acid (CAS Registry No. 42137-76-8), 3-dibenzofuransulfonic acid (CAS Registry No. 215189-98-3), 1-ethylquinaldinium iodide (CAS Registry No. 606-53-3), fluorescein (CAS Registry No. 2321-07-5), fluorescein, sodium salt (CAS Registry No. 518-47-8, aka Acid Yellow 73, Uranine), Keyfluor White ST (CAS Registry No. 144470-48-4, aka Flu. Bright 28), benzenesulfonic acid, 2,2'-(1,2-ethenediyl)bis[5-[[4-[bis(2-hydroxyethyl)amino]-6-[(4-sulfophenyl)amino]-1,3,5-triazin-2-yl]amino]-, tetrasodium salt, also known as Keyfluor White CN (CAS Registry No. 16470-24-9), C.I. Fluorescent Brightener 230, also known as Leucophor BSB (CAS Registry No. 68444-86-0), benzenesulfonic acid, 2,2'-(1,2-ethenediyl)bis [5-[[4-[bis(2-hydroxyethyl)amino]-6-[(4-sulfophenyl) amino]-1,3,5-triazin-2-yl]amino]-, tetrasodium salt, also known as Leucophor BMB (CAS Registry No. 16470-24-9, aka Leucophor U, Flu. Bright. 290), 9,9'-biacridinium, 10,10'-dimethyl-, dinitrate, also known as Lucigenin (CAS Registry No. 2315-97-1, aka bis-N-methylacridinium nitrate), 1-deoxy-1-(3,4-dihydro-7,8-dimethyl-2,4-dioxobenzo[g]pteridin-10(2H)-yl)-D-ribitol, also known as Riboflavin or Vitamin B2 (CAS Registry No. 83-88-5), mono-, di-, or tri-sulfonated napthalenes, including but not limited to 1,5-naphthalenedisulfonic acid, disodium salt (hydrate) (CAS Registry No. 1655-29-4, aka 1,5-NDSA hydrate), 2-amino-1-naphthalenesulfonic acid (CAS Registry No. 81-16-3), 5-amino-2-naphthalenesulfonic acid (CAS Registry No. 119-79-9), 4-amino-3-hydroxy-1-naphthalenesulfonic acid (CAS Registry No. 90-51-7), 6-amino-4-hydroxy-2-naphthalenesulfonic acid (CAS Registry No. 116-63-2), 7-amino-1,3-naphthalenesulfonic acid, potassium salt (CAS Registry No. 79873-35-1), 4-amino-5-hydroxy-2,7-naphthalenedisulfonic acid (CAS Registry No. 90-20-0), 5-dimethylamino-1-naphthalenesulfonic acid (CAS Registry No. 4272-77-9), 1-amino-4-naphthalene sulfonic acid (CAS Registry No. 84-86-6), 1-amino-7-naphthalene sulfonic acid (CAS Registry No. 119-28-8), 2,6-naphthalenedicarboxylic acid, dipotassium salt (CAS Registry No. 2666-06-0), 3,4,9,10-perylenetetracarboxylic acid (CAS Registry No. 81-32-3), C.I. Fluorescent Brightener 191, also known as Phorwite CL (CAS Registry No. 12270-53-0), C.I. Fluorescent Brightener 200, also known as Phorwite BKL (CAS Registry No. 61968-72-7), benzenesulfonic acid, 2,2'-(1,2-ethenediyl)bis[5-(4-phenyl-2H-1,2,3-triazol-2-yl)-, dipotassium salt, also known as Phorwite BHC 766 (CAS Registry No. 52237-03-3), benzenesulfonic acid, 5-(2H-naphtho[1,2-d]triazol-2-yl)-2-(2-phenylethenyl)-, sodium salt, also known as Pylaklor White S-15A (CAS Registry No. 6416-68-8), 1,3,6,8-pyrenetetrasulfonic acid, tetrasodium salt (CAS Registry No. 59572-10-0), pyranine, (CAS Registry No. 6358-69-6, aka 8-hydroxy-1,3,6-pyrenetrisulfonic acid, trisodium salt), quinoline (CAS Registry No. 91-22-5), 3H-phenoxazin-3-one, 7-hydroxy-, 10-oxide, also known as Rhodalux (CAS Registry No. 550-82-3), xanthylium, 9-(2,4-dicarboxyphenyl)-3,6-bis(diethylamino)-, chloride, disodium salt, also known as Rhodamine WT (CAS Registry No. 37299-86-8), phenazinium, 3,7-diamino-2,8-dimethyl-5-phenyl-, chloride, also known as Safranine O (CAS Registry No. 477-73-6), C.I. Fluorescent Brightener 235, also known as Sandoz CW (CAS Registry No. 56509-06-9), benzenesulfonic acid, 2,2'-(1,2-ethenediyl)bis[5-[[4-[bis(2-hydroxyethyl)amino]-6-[(4-sulfophenyl)amino]-1,3,5-triazin-2-yl]amino]-, tetrasodium salt, also known as Sandoz CD (CAS Registry No. 16470-24-9, aka Flu. Bright. 220), benzenesulfonic acid, 2,2'-(1,2-ethenediyl)bis[5-[[4-[(2-hydroxypropyl)amino]-6-(phenylamino)-1,3,5-triazin-2-yl]amino]-, disodium salt, also known as Sandoz TH-40 (CAS Registry No. 32694-95-4), xanthylium, 3,6-bis(diethylamino)-9-(2,4-disulfophenyl)-, inner salt, sodium salt, also known as Sulforhodamine B (CAS Registry No. 3520-42-1, aka Acid Red 52), benzenesulfonic acid, 2,2'-(1,2-ethenediyl)bis[5-[[4-[(aminomethyl)(2-hydroxyethyl)amino]-6-(phenylamino)-1,3,5-triazin-2-yl]amino]-, disodium salt, also known as Tinopal 5BM-GX (CAS Registry No. 169762-28-1), Tinopol DCS (CAS Registry No. 205265-33-4), benzenesulfonic acid, 2,2'-([1,1'-biphenyl]-4,4'-diyldi-2,1-ethenediyl)bis-, disodium salt also known as Tinopal CBS-X (CAS Registry No. 27344-41-8), benzenesulfonic acid, 5-(2H-naphtho[1,2-d]triazol-2-yl)-2-(2-phenylethenyl)-, sodium salt, also known as Tinopal RBS 200, (CAS Registry No. 6416-68-8), 7-benzothiazolesulfonic acid, 2,2'-(1-triazene-1,3-diyldi-4,1-phenylene)bis[6-methyl-, disodium salt, also known as Titan Yellow (CAS Registry No. 1829-00-1, aka Thiazole Yellow G), and all ammonium, potassium and sodium salts thereof, and all like agents and suitable mixtures thereof.

Preferred tracers include 1-deoxy-1-(3,4-dihydro-7,8-dimethyl-2,4-dioxobenzo[g]pteridin-10(2H)-yl)-D-ribitol, also known as Riboflavin or Vitamin B2 (CAS Registry No. 83-88-5), fluorescein (CAS Registry No. 2321-07-5), fluorescein, sodium salt (CAS Registry No. 518-47-8, aka Acid Yellow 73, Uranine), 2-anthracenesulfonic acid sodium salt (CAS Registry No. 16106-40-4), 1,5-anthracenedisulfonic acid (CAS Registry No. 61736-91-[2]) and salts thereof, 2,6-anthracenedisulfonic acid (CAS Registry No. 61736-95-6) and salts thereof, 1,8-anthracenedisulfonic acid (CAS Registry No. 61736-92-3) and salts thereof, mono-, di-, or tri-sulfonated napthalenes, including but not limited to 1,5-naphthalenedisulfonic acid, disodium salt (hydrate) (CAS Registry No. 1655-29-4, aka 1,5-NDSA hydrate), 2-amino-1-naphthalenesulfonic acid (CAS Registry No. 81-16-3), 5-amino-2-naphthalenesulfonic acid (CAS Registry No. 119-79-9), 4-amino-3-hydroxy-1-naphthalenesulfonic acid (CAS Registry No. 90-51-7), 6-amino-4-hydroxy-2-naphthalenesulfonic acid (CAS Registry No. 116-63-2), 7-amino-1,3-naphthalenedisulfonic acid, potassium salt (CAS Registry No.79873-35-1), 4-amino-5-hydroxy-2,7-naphthalenedisulfonic acid (CAS Registry No. 90-20-0), 5-dimethylamino-1-naphthalenesulfonic acid (CAS Registry No. 4272-77-9), 1-amino-4-naphthalene sulfonic acid (CAS Registry No. 84-86-6), 1-amino-7-naphthalene sulfonic acid (CAS Registry No. 119-28-8), 2,6-naphthalenedicarboxylic acid, dipotassium salt (CAS Registry No. 2666-06-0), 3,4,9,10-perylenetetracarboxylic acid (CAS Registry No. 81-32-3), C.I. Fluorescent Brightener 191, also known as, Phorwite CL (CAS Registry No. 12270-53-0), C.I. Fluorescent Brightener 200, also known as Phorwite BKL (CAS Registry No. 61968-72-7), benzenesulfonic acid, 2,2'-(1,2-ethenediyl)bis[5-(4-phenyl-2H-1,2,3-triazol-2-yl)-dipotassium salt, also known as Phorwite BHC 766 (CAS Registry No. 52237-03-3), benzenesulfonic acid, 5-(2H-naphtho[1,2-d]triazol-2-yl)-2-(2-phenylethenyl)-, sodium salt, also known as Pylaklor White S-15A (CAS Registry No. 6416-68-8), pyranine, (CAS Registry No. 6358-69-6, aka 8-hydroxy-1,3,6-pyrenetrisulfonic acid, trisodium salt), quinoline (CAS Registry No. 91-22-5), 3H-phenoxazin-3-one, 7-hydroxy-, 10-oxide, also known as Rhodalux (CAS Registry No. 550-82-3), xanthylium, 9-(2,4-dicarboxyphenyl)-3,6-bis(diethylamino)-, chloride, disodium salt, also known as Rhodamine WT (CAS Registry No. 37299-86-8), phenazinium, 3,7-diamino-2,8-dimethyl-5-phenyl-, chloride, also known as Safranine O (CAS Registry No. 477-73-6), C.I. Fluorescent Brightener 235, also known as Sandoz CW (CAS Registry No. 56509-06-9), benzenesulfonic acid, 2,2'-(1,2-ethenediyl)bis[5-[[4-[bis(2-hydroxyethyl)amino]-6-[(4-sulfophenyl)amino]-1,3,5-triazin-2-yl]amino]-, tetrasodium salt, also known as Sandoz CD (CAS Registry No. 16470-24-9, aka Flu. Bright. 220), benzenesulfonic acid, 2,2'-(1,2-ethenediyl)bis[5-[[4-[(2-hydroxypropyl)amino]-6-(phenylamino)-1,3,5-triazin-2-yl]amino]-, disodium salt, also known as Sandoz TH-40 (CAS Registry No. 32694-95-4), xanthylium, 3,6-bis(diethylamino)-9-(2,4-disulfophenyl)-, inner salt, sodium salt, also known as Sulforhodamine B (CAS Registry No. 3520-42-1, aka Acid Red 52), benzenesulfonic acid, 2,2'-(1,2-ethenediyl)bis[5-[[4-[(aminomethyl)(2-hydroxyethyl)amino]-6-(phenylamino)-1,3,5-triazin-2-yl]amino]-, disodium salt, also known as Tinopal 5BM-GX (CAS Registry No. 169762-28-1), Tinopol DCS (CAS Registry No. 205265-33-4), benzenesulfonic acid, 2,2'-([1,1'-biphenyl]-4,4'-diyldi-2,1-ethenediyl)bis-, disodium salt, also known as Tinopal CBS-X (CAS Registry No. 27344-41-8), benzenesulfonic acid, 5-(2H-naphtho[1,2-d]triazol-2-yl)-2-(2-phenylethenyl)-, sodium salt, also known as Tinopal RBS 200, (CAS Registry No. 6416-68-8), 7-benzothiazolesulfonic acid, 2,2'-(1-triazene-1,3-diyldi-4,1-phenylene)bis[6-methyl-, disodium salt, also known as Titan Yellow (CAS Registry No. 1829-00-1, aka Thiazole Yellow G), and all ammonium, potassium and sodium salts thereof, and all like agents and suitable mixtures thereof.

More preferred fluorescent tracers include fluorescein, sodium salt (CAS Registry No. 518-47-8, aka Acid Yellow 73, Uranine); 1,5-naphthalenedisulfonic acid disodium salt (hydrate) (CAS Registry No. 1655-29-4, aka 1,5-NDSA hydrate); xanthylium, 9-(2,4-dicarboxyphenyl)-3,6-bis(diethylamino)-, chloride, disodium salt, also known as Rhodamine WT (CAS Registry No. 37299-86-8); 1-deoxy-1-(3,4-dihydro-7,8-dimethyl-2,4-dioxobenzo[g]pteridin-10(2H)-yl)-D-ribitol, also known as Riboflavin or Vitamin B2 (CAS Registry No. 83-88-5); fluorescein (CAS Registry No. 2321-07-5); 2-anthracenesulfonic acid sodium salt (CAS Registry No. 16106-40-4); 1,5-anthracenedisulfonic acid (CAS Registry No. 61736-91-2) and salts thereof; 2,6-anthracenedisulfonic acid (CAS Registry No. 61736-95-6) and salts thereof; 1,8-anthracenedisulfonic acid (CAS Registry No. 61736-92-3) and salts thereof; and mixtures thereof. The fluorescent tracers listed above are commercially available from a variety of different chemical supply companies.

In addition to the tracers listed above, those skilled in the art will recognize that salts using alternate counter ions may also be used. Thus, for example, anionic tracers, which have Na+ as a counter ion, could also be used in forms where the counter ion is chosen from $K^+$, $Li^+$, $NH_4^+$, $Ca^{+2}$, $Mg^{+2}$ or other appropriate counter ions. Similarly, cationic tracers may have a variety of counter ions, for example: $Cl^-$, $SO_4^{-2}$, $PO_4^{-3}$, $HPO_4^{-2}$; $H_2PO_4^-$; $CO_3^{-2}$; $HCO_3^-$; or other appropriate counter ions.

In an embodiment, the treating agent is tagged with a fluorescent moiety, for example by incorporating the fluorescent moiety into a polymeric treatment polymer itself, or by post modification of a treatment polymer with a fluorescent moiety capable of forming a covalent bond with the treatment polymer. The preparation and use of polymers containing a fluorescent moiety is described in, for example, U.S. Pat. Nos. 6,312,644; 6,077,461; 5,986,030; 5,998,632; 5,808,103; 5,772,894; 5,958,788 and PCT U.S. Ser. No. 01/81654, incorporated herein by reference.

The dosage of the fluorescent tracer is an amount that is at least sufficient to provide a measurable concentration in the treated water. Typical doses range from about 50 ppt (parts per trillion) to about 100 ppb (parts per billion), preferably from about 0.1 ppb to about 10 ppb, based on fluorescent agent concentration. Note that 50 ppt is about the detection limit of currently available industrial fluorometers. Improvements in fluorometer technology are likely to reduce this detection limit and are envisioned.

The fluorescent tracers can be detected by utilizing a variety of different and suitable techniques. For example, fluorescence emission spectroscopy on a substantially continuous basis, at least over a given time period, is one of the preferred analytical techniques according to an embodiment of this invention. One method for the continuous on-stream measuring of chemical tracers by fluorescence emission spectroscopy and other analysis methods is described in U.S. Pat. No. 4,992,380, incorporated herein by reference.

Examples of fluorometers that may be used in the practice of this invention include the Xe II and TRASAR® 8000 fluorometer (available from Nalco Company, Naperville, Ill.); the Hitachi F-4500 fluorometer (available from Hitachi through Hitachi Instruments Inc., San Jose, Calif.); the JOBIN YVON FluoroMax-3 "SPEX" fluorometer (available from JOBIN YVON Inc., Edison, N.J.); and the Gilford Fluoro-IV spectrophotometer or the SFM 25 (available from Bio-tech Kontron through Research Instruments International, San Diego, Calif.). It should be appreciated that the foregoing list is not comprehensive and is intended only to show examples of representative fluorometers. Other commercially available fluorometers and modifications thereof can also be used in this invention.

It should be appreciated that a variety of other suitable analytical techniques may be utilized to measure the amount of fluorescent tracers. Examples of such techniques include combined HPLC-fluorescence analysis, colorimetry analysis, ion selective electrode analysis, transition metal analysis, chemiluminescence, pulsed fluorescence measurements, and the like.

In an embodiment, the present invention includes a controller programmed with the foregoing algorithm and which continuously (i.e. within the timescale of the retention time, typically every few minutes) makes incremental changes in the treating agent dosage and performs the calculations described above so as to maintain the treating agent residuals at the desired set point.

The controller can be configured and/or adjusted in a variety of different and suitable ways. Alternative methods could include using three or more points to measure the fluorescence response and then use analytical curve fitting methods to determine optimal dosage.

The controller can be either hard wired (e.g., electrical communication cable), or can communicate with the other components described herein by wireless communication (e.g., wireless RF interface), a pneumatic interface and the like.

As described above, this invention is a method of monitoring treating agent residuals and controlling treating agent dosage in water treatment processes. "Treating agent" is meant herein without limitation to include treatment chemicals that enhance solid-liquid separation, membrane separation process performance, antiscalants that retard/prevent scale formation and deposition on surfaces in contact with the treated water, antifoulants that retard/prevent membrane fouling, biodispersants, microbial-growth inhibiting agents such as biocides and cleaning chemicals that remove deposits from surfaces that contact the treated water.

The present invention is applicable to all industries that can employ water treatment processes. For example, the different types of industrial processes in which the method of the present invention can be applied generally include raw water processes, waste water processes, industrial water processes, municipal water treatment, food and beverage processes, pharmaceutical processes, electronic manufacturing, utility operations, pulp and paper processes, mining and mineral processes, transportation-related processes, textile processes, plating and metal working processes, laundry and cleaning processes, leather and tanning processes, and paint processes.

In particular, food and beverage processes can include, for example, dairy processes relating to the production of cream, low-fat milk, cheese, specialty milk products, protein isolates, lactose manufacture, whey, casein, fat separation, and brine recovery from salting cheese. Uses relating to the beverage industry including, for example, fruit juice clarification, concentration or deacidification, alcoholic beverage clarification, alcohol removal for low-alcohol content beverages, process water; and uses relating to sugar refining, vegetable protein processing, vegetable oil production/processing, wet milling of grain, animal processing (e.g., red meat, eggs, gelatin, fish and poultry), reclamation of wash waters, food processing waste and the like.

Examples of industrial water uses as applied to the present invention include, for example, boiler water production, process water purification and recycle/reuse, softening of raw water, treatment of cooling water blow-down, reclamation of water from papermaking processes, desalination of sea and brackish water for industrial and municipal use, drinking/raw/surface water purification including, for example, the use of membranes to exclude harmful micro-organisms from drinking water, polishing of softened water, membrane bio-reactors, mining and mineral process waters.

Examples of waste water treatment applications with respect to the method of this invention include, for example, industrial waste water treatment, biological-waste treatment systems, removal of heavy metal contaminants, polishing of tertiary effluent water, oily waste waters, transportation related processes (e.g., tank car wash water), textile waste (e.g., dye, adhesives, size, oils for wool scouring, fabric finishing oils), plating and metal working waste, laundries, printing, leather and tanning, pulp and paper (e.g., color removal, concentration of dilute spent sulfite liquor, lignin recovery, recovery of paper coatings), chemicals (e.g., emulsions, latex, pigments, paints, chemical reaction by-products), and municipal waste water treatment (e.g., sewage, industrial waste).

Other examples of industrial applications of the present invention include, for example, semiconductor rinse water processes, production of water for injection, pharmaceutical water including water used in enzyme production/recovery and product formulation, and electro-coat paint processing.

In an embodiment, the present invention is applied in raw or treated water applications where the filtrate is used as feed for reverse osmosis units. It is particularly important that polymer residuals not foul RO membranes, although the present invention is envisioned for any application where the use pretreatment polymers is desired, but excessive polymer residuals are not, as well as applications that benefit from control of treating agent dosing. Some examples would be, surface water clarification, ground water clarification, tertiary treatment of wastewater, and seawater clarification. The product of such clarification processes could be used for, but not limited to, industrial process water, boiler or cooling water make-up water, or residential water.

In an embodiment, the water treatment process is a solid-liquid separation process.

In an embodiment, the solid-liquid separation process comprises treatment of the water with one or more coagulants or flocculants, or a combination thereof, to form a mixture of water and coagulated and flocculated solids and separation of the coagulated and flocculated solids from the water.

Suitable flocculatants include high molecular weight cationic, anionic, nonionic, zwitterionic or amphoteric polymers. Suitable flocculants generally have molecular weights in excess of 1,000,000 and often in excess of 5,000,000. The polymeric flocculant is typically prepared by vinyl addition polymerization of one or more cationic, anionic or nonionic monomers, by copolymerization of one or more cationic monomers with one or more nonionic monomers, by copolymerization of one or more anionic monomers with one or more nonionic monomers, by copolymerization of one or more cationic monomers with one or more anionic monomers and optionally one or more nonionic monomers to produce an amphoteric polymer or by polymerization of one or more zwitterionic monomers and optionally one or more nonionic monomers to form a zwitterionic polymer. One or more zwitterionic monomers and optionally one or more nonionic monomers may also be copolymerized with one or more anionic or cationic monomers to impart cationic or anionic charge to the zwitterionic polymer.

While cationic polymer flocculants may be formed using cationic monomers, it is also possible to react certain nonionic vinyl addition polymers to produce cationically charged polymers. Polymers of this type include those prepared through the reaction of polyacrylamide with dimethylamine and formaldehyde to produce a Mannich derivative.

Similarly, while anionic polymer flocculants may be formed using anionic monomers, it is also possible to modify certain nonionic vinyl addition polymers to form anionically charged polymers. Polymers of this type include, for example, those prepared by the hydrolysis of polyacrylamide.

The flocculants may be used in the solid form, as an aqueous solution, as a water-in-oil emulsion, or as dispersion in water. Representative cationic polymers include copolymers and terpolymers of (meth)acrylamide with dimethylaminoethyl methacrylate (DMAEM), dimethylaminoethyl acrylate (DMAEA), diethylaminoethyl acrylate (DEAEA), diethylaminoethyl methacrylate (DEAEM) or their quaternary ammonium forms made with dimethyl sulfate, methyl chloride or benzyl chloride.

Water-soluble coagulants are well known and commercially available. Suitable coagulants may be inorganic or organic. Representative inorganic coagulants include alum, sodium aluminate, polyaluminum chlorides or PACls(which also may be also be referred to as aluminum chlorohydroxide, aluminum hydroxide chloride, basic aluminum chloride and polyaluminum hydroxychloride, and the like), sulfated polyaluminum chlorides, polyaluminum silica sulfate, ferric sulfate, ferric chloride, and the like and blends thereof.

Many water-soluble organic coagulants are formed by condensation polymerization. Examples of polymers of this type include epichlorohydrin-dimethylamine, and epichlorohydrin-dimethylamine-ammonia polymers.

Additional coagulants include polymers of ethylene dichloride and ammonia, or ethylene dichloride and dimethylamine, with or without the addition of ammonia, condensation polymers of multifunctional amines such as diethylenetriamine, tetraethylenepentamine, hexamethylenediamine and the like with ethylenedichloride and polymers made by condensation reactions such as melamine formaldehyde resins.

Additional coagulants include cationically charged vinyl addition polymers such as polymers and copolymers of diallyldimethylammonium chloride, dimethylaminoethylmethacrylate, dimethylaminoethylmethacrylate methyl chloride quaternary salt, methacrylamidopropyltrimethylammonium chloride, (methacryloxyloxyethyl)trimethyl ammonium chloride, diallylmethyl(beta-propionamido)ammonium chloride, (beta-methacryloxyloxyethyl)trimethyl-ammonium methylsulfate, quaternized polyvinyllactam, dimethylamino-ethylacrylate and its quaternary ammonium salts, vinylamine and acrylamide or methacrylamide which has been reacted to produce the Mannich or quaternary Mannich derivatives. The molecular weights of these cationic polymers, both vinyl addition and condensation, range from as low as several hundred to as high as one million. Preferably, the molecular weight range should be from about 20,000 to about 1,000,000.

The selection of the proper flocculant and coagulant for a particular application and determination of the effective dose may be empirically determined by one of skill in the art of water treatment based on the characteristics of the particular water being treated.

The coagulated and flocculated solids may then be separated from the water by any of a number of means available in the art of solid-liquid separation including clarifiers, by centrifuges, dissolved air flotation, mechanical means such as belt press or plate and frame press, and membrane filtration or media filtration. Membrane filtration is generally considered micro or ultra filtration involving pliable membranes, ceramic membranes and the like. Media filtration is generally considered to be any granular media involved as a barrier to contaminants in water and they are commonly sand, anthracite, and garnet. Any media that functions as a barrier is envisions and this includes, but not limited to, micro and macro breads, powders, activated carbon, ceramics, etc.

In an embodiment, the solid-liquid separation process is a membrane separation process wherein the coagulated and flocculated solids are separated from the water by filtration through a membrane.

Membrane separations commonly used for water purification or other liquid processing include microfiltration (MF), ultrafiltration (UF), nanofiltration (NF), reverse osmosis (RO), electrodialysis, electrodeionization, pervaporation, membrane extraction, membrane distillation, membrane stripping, membrane aeration, and other processes. The driving force of the separation depends on the type of the membrane separation. Pressure-driven membrane filtration, also known as membrane filtration, includes microfiltration, ultrafiltration, nanofiltration and reverse osmosis, and uses pressure as a driving force, whereas the electrical driving force is used in electrodialysis and electrodeionization.

In an embodiment, the membrane separation process comprises one or more pretreatment steps wherein a portion of the coagulated and flocculated solids are separated from the water prior to filtration of the water through a nanofiltration and/or reverse osmosis membrane.

In an embodiment, the membrane separation system is a reverse osmosis system.

In reverse osmosis, the feed stream is typically processed under cross flow conditions. In this regard, the feed stream flows substantially parallel to the membrane surface such that only a portion of the feed stream diffuses through the membrane as permeate. The cross flow rate is routinely high in order to provide a scouring action that lessens membrane surface fouling. This can also decrease concentration polarization effects (e.g., concentration of solutes in the reduced-turbulence boundary layer at the membrane surface, which can increase the osmotic pressure at the membrane and thus can reduce permeate flow). The concentration polarization effects can inhibit the feed stream water from passing through the membrane as permeate, thus decreasing the recovery ratio, e.g., the ratio of permeate to applied feed stream. A recycle loop(s) may be employed to maintain a high flow rate across the membrane surface.

Reverse osmosis processes can employ a variety of different types of membranes. Such commercial membrane element types include, without limitation, hollow fiber membrane elements, tubular membrane elements, spiral-wound membrane elements, plate and frame membrane elements, and the like, some of which are described in more detail in "The Nalco Water Handbook," Second Edition, Frank N. Kemmer ed., McGraw-Hill Book Company, New York, N.Y., 1988, incorporated hereinto, particularly Chapter 15 entitled "Membrane Separation". It should be appreciated that a single membrane element may be used in a given membrane filtration system, but a number of membrane elements can also be used depending on the industrial application.

A typical reverse osmosis system is described as an example of membrane filtration and more generally membrane separation. Reverse osmosis uses mainly spiral wound elements or modules, which are constructed by winding layers of semi-porous membranes with feed spacers and permeate water carriers around a central perforated permeate collection tube. Typically, the modules are sealed with tape and/or fiberglass over-wrap. The resulting construction has one channel, which can receive an inlet flow. The inlet stream flows longitudinally along the membrane module and exits the other end as a concentrate stream. Within the module, water passes through the semi-porous membrane and is trapped in a permeate channel which flows to a central collection tube. From this tube it flows out of a designated channel and is collected.

In practice, membrane modules are stacked together, end-to-end, with inter-connectors joining the permeate tubes of the first module to the permeate tube of the second module, and so on. These membrane module stacks are housed in pressure vessels. Within the pressure vessel feed water passes into the first module in the stack, which removes a portion of the water as permeate water. The concentrate stream from the first membrane becomes the feed stream of the second membrane and so on down the stack. The permeate streams from all of the membranes in the stack are collected in the joined permeate tubes.

Within most reverse osmosis systems, pressure vessels are arranged in either "stages" or "passes." In a staged membrane system, the combined concentrate streams from a bank of pressure vessels are directed to a second bank of pressure vessels where they become the feed stream for the second stage. Commonly systems have 2 to 3 stages with successively fewer pressure vessels in each stage. For example, a system may contain 4 pressure vessels in a first stage, the concentrate streams of which feed 2 pressure vessels in a second stage, the concentrate streams of which in turn feed 1 pressure vessel in the third stage. This is designated as a "4:2:1" array. In a staged membrane configuration, the combined permeate streams from all pressure vessels in all stages are collected and used without further membrane treatment. Multi-stage systems are used when large volumes of purified water are required. The permeate streams from the membrane system may be further purified by ion exchange or other means.

In a multi-pass system, the permeate streams from each bank of pressure vessels are collected and used as the feed to the subsequent banks of pressure vessels. The concentrate streams from all pressure vessels are combined without further membrane treatment of each individual stream. Multi-pass systems are used when very high purity water is required, for example in the microelectronics or pharmaceutical industries.

It is well known to those skilled in the art, that various coagulants are needed to maximize the efficiency of solid-liquid separation. As noted above, amongst these suitable coagulants are aluminum and iron compounds and synthetic polyelectrolytes. Unfortunately, using aluminum, such as alum, produces residuals that form intractable scale on membranes. Polyelectrolytes are frequently used for general clarification, but since RO membranes are anionic polyamide films and polyelectrolyte coagulants are cationic, it is widely feared that polymer will deposit on membranes via electrostatic attraction and cause permanent fouling. This situation would require expensive, inefficient membrane replacement. Therefore, in reverse osmosis filtration systems, pretreatment is critical to efficient operation.

Accordingly, in an embodiment, this invention is a method of monitoring filter aid residuals in treated water in a reverse osmosis pretreatment program wherein the water is treated with one or more filter aids to form a mixture of coagulated and flocculated solids and at least a portion of the coagulated and flocculated solids are removed from the water, using micro or ultra or media filtration, prior to filtration through a reverse osmosis membrane comprising i) adding a first dose of a filter aid traced or tagged with a fluorescent tracer to a first sample of the water to form a mixture comprising water, coagulated and flocculated solids and filter aid traced or tagged with a fluorescent tracer;

ii) separating at least a portion of the coagulated and flocculated solids from the first sample of the water;

iii) measuring the concentration of the fluorescent tracer in the first sample of the water;

iv) adding a second dose of the filter aid traced or tagged with the fluorescent tracer to a second sample of the water to form a second mixture comprising water, coagulated and flocculated solids and filter aid traced or tagged with a fluorescent tracer;

v) separating at least a portion of the coagulated and flocculated solids from the second sample of the water;

vi) measuring the concentration of the fluorescent tracer in the second sample of the water; and vii) correlating the change in the measured concentration of the fluorescent tracer at the respective treating agent doses to the residual concentration of the filter aid.

Reverse osmosis pretreatment schemes will vary with the type of water. For example, waters that have greater than ca.

10 NTU will usually utilize sedimentation followed by filtration. Waters that are cleaner than ca. 10 NTU can use direct filtration techniques.

Filtration generally consists of a media filter or a membrane micro or ultrafilter. Media filters consist of particulate solids on the order of 1 mm diameter. While a wide variety of materials can be used, the most common materials are sand, garnet and anthracite singly or in combination. Micro and ultrafilters can consist of either ceramic or membrane construction and have significantly smaller pore size compared to media filters. All three of these types are used for RO pretreatment.

Various coagulants can be used as filter aids in RO pretreatment. Filter aids function by modifying the influent particle size and surface properties in order to facilitate particulate capture by the filter. Which type of filter aid to use varies from water to water and for optimal filtration, the proper chemistry, or even mix of chemistries, is critical.

In an embodiment, this invention is a reverse osmosis pretreatment system wherein the residual concentration of the filter aid is correlated with the change in measured concentration of the fluorescent tracer at the respective treating agent doses using a function of the difference between molecules of fluorescent tracer added to the water and molecules of fluorescent tracer detected in the water.

In an embodiment, this invention is a reverse osmosis pretreatment system wherein the residual concentration of the filter aid is correlated with the change in measured concentration of the fluorescent tracer at the respective treating agent doses using a function of the difference between the fluorescence quenching expected and the fluorescence quenching detected.

In an embodiment, this invention is a reverse osmosis pretreatment system wherein the residual concentration of the filter aid is correlated with filter aid dosage.

In an embodiment, this invention is a reverse osmosis pretreatment system wherein the residual concentration of the filter aid is used to determine an upper and lower limit of treating dosage.

In an embodiment, this invention is a reverse osmosis pretreatment system wherein the filter aid dosage is automatically maintained between the upper and lower limit.

In an embodiment, this invention is a reverse osmosis pretreatment system wherein the filter aid is tagged with a fluorescent tracer.

In an embodiment, this invention is a reverse osmosis pretreatment system wherein the filter aid is traced with a fluorescent tracer.

In an embodiment, this invention is a reverse osmosis pretreatment system wherein the portion of coagulated and flocculated solids is removed from the water by filtration through a media filter.

In an embodiment, this invention is a reverse osmosis pretreatment system wherein the filter aid is one or more coagulants selected from alum, polyaluminum chloride, ferric chloride, ferric sulfate, poly(diallyldimethylammonium chloride) and Epi-DMA.

In an embodiment, this invention is a reverse osmosis pretreatment system wherein the fluorescent tracer is selected from fluorescein, rhodamine B, rhodamine WT and 1,3,6,8-pyrenetetrasulfonic acid tetrasodium salt.

In an embodiment, this invention is a reverse osmosis pretreatment system wherein the fluorescent tracer is poly(diallyldimethylammonium chloride) tagged with luminol, rhodamine or fluorescein.

The foregoing may be better understood by reference to the following examples, which are presented for purposes of illustration and are not intended to limit the scope of the invention.

EXAMPLE 1

As discussed above, the optimal treating agent dosage is calculated using the inverse derivative of fluorescence response with respect to treating agent dose and correlating to a water quality parameter, in this case turbidity, using standard jar test methods to measure fluorescence and turbidity.

For purposes of this example, jar tests are accomplished using a four-unit jar tester from A&F Machine Products Co., Berea, Ohio (model number "JAR MIXER") according to the following protocol.

1) Place a 250-1,000 mL test sample in a sample jar and initiate stirring at 200 rpm.
2) Add treating agent via syringe into the vortex of the stirred sample and continue stirring for 30 seconds.
3) Slow the stirring to 15 to 60 rpm and continue stirring for 5 minutes.
4) Stop stirring, remove the paddles from the sample and allow the sample to settle for 5 minutes.
5) Remove a sample of the supernatant via pipette or syringe from a level about 1 cm below the sample surface and filter the sample through a 5 μm syringe filter directly into the turbidity and fluorescence sample cells for measurement of the appropriate property.

The treating agent promotes the agglomeration of smaller particles into larger particles, or flocs, that can be more readily separated from the water, for example by settling or filtration. In the event that visible flocs are formed, the floc size of the average particle formed may be ranked versus the benchmark. Other factors such as water clarity between floc particles, floc shape, tightness, etc. may also be noted for comparison.

All jar tests should be benchmarked using a plant's current coagulation program. This allows for adjustment of testing parameters to correlate with full-scale performance. The actual dose in use in the plant at the time of the tests is set as the dose benchmark for the series of tests and the clarifier overflow turbidity (or color, etc.) is the performance benchmark.

The parameters of the jar test can be varied based on the treatment application and characteristics of the samples being tested. Accordingly, alternative methods may employ a longer fast mix of 1 to 5 minutes and a slow mix of 2-10 minutes with or without a settling stage. For example, if alum is added at the intake and travels a long distance, then the fast mix will be longer than if alum is added only 20 feet before the clarifier. A plant that is hydrologically overloaded will need a slow mix shorter slow mix. These factors are varied based on experience of treatment personnel.

For this example 1, Mississippi River water is jar tested using 30 ppm of a 50 weight percent ferric sulfate solution and augmenting the ferric sulfate coagulant with a fluorescein-traced poly(diallyldimethylammonium chloride) ("polyDADMAC") coagulant. The polyDADMAC is approximately 20-weight percent polymer and 0.19 weight percent fluorescein with the balance being an approximately one weight percent saline solution. The polyDADMAC solution concentration is listed in Table 1 in ppm on a weight/weight ("w/w") basis. The performance metrics are turbidity in NTU and detected fluorescein fluorescence in ppb (w/w) of fluorescein in the filtrate. The Fluorometer is a Hitachi Model F-4500 and calibration is accomplished using fluorescein in deionized water. A Hach portable turbidimeter Model 2100P is used for NTU measurements. The results are summarized in Table 1.

TABLE 1

| ppm | 1/ppm | Settled NTU | Fluorescence Intensity, ppb | Quenching |
|---|---|---|---|---|
| 1 | 1.00000 | 10.9 | 2.08 | 0.48077 |
| 5 | 0.20000 | 4.3 | 8.65 | 0.11561 |
| 9 | 0.11111 | 5.0 | 15.3 | 0.06536 |
| 13 | 0.07692 | 6.9 | 21.9 | 0.04566 |
| 17 | 0.05882 | 11.0 | 27.3 | 0.03663 |

In Table 1, the last column is quenching which is analytically calculated as the inverse of the fluorescence. Therefore the quenching has units of $ppb^{-1}$. Note that the fluorescence units can be arbitrary and for the purposes of the invention, only relative fluorescence intensity is required.

EXAMPLE 2

Testing is also accomplished in the field according to the method of Example 1 using the Hach 2100P turbidimeter on Mississippi River water that has been previously treated for turbidity removal resulting in a turbidity of about 1 NTU. Fluorescence data is obtained using a TRASAR 8000 Fluorometer from Nalco Company, Naperville, Ill. The TRASAR 8000 requires a correction at zero added fluorescein with the correction being a subtraction of 0.06 ppb fluorescein. This correction is attributed to less precise optics versus the research grade Hitachi. PolyDADMAC is the treating agent. The fast mix is 30 seconds, slow mix three minutes and settling time five minutes. The Fluorescence Intensity, ppb is without the 0.06 ppb fluorescein background correction, while the Corrected Quenching is the inverse of the corrected Fluorescence Intensity, so it has units of $ppb^{-1}$. The results are shown in Table 2

TABLE 2

| ppm | 1/ppm | 5 um Filtered NTU | Fluorescence Intensity, ppb | Corrected Quenching |
|---|---|---|---|---|
| 0.4 | 2.5000 | 0.30 | 0.1140 | 18.5185 |
| 0.6 | 1.6667 | 0.43 | 0.1470 | 11.4943 |
| 0.8 | 1.2500 | 0.69 | 0.1650 | 9.5238 |
| 1.0 | 1.0000 | 0.50 | 0.3300 | 3.7037 |

Note that in Table 2, 0.06 ppb is subtracted to correct the fluorescence.

EXAMPLE 3

Natural surface water from a lake in Montana, USA, is treated with a dual filter aid program using ferric sulfate solution and polyDADMAC, as summarized in Table 3. The fast mix is two minutes, slow mix ten minutes and no settling time and the 0.057 ppb fluorescein correction is subtracted from the measured fluorescence intensity. The results are summarized in Table 3.

TABLE 3

| ppm | 1/ppm | 5 um Filtered NTU | Fluorescence Intensity, ppb | Corrected Quenching |
|---|---|---|---|---|
| 0.50 | 2.0000 | 1.05 | 0.408 | 2.8490 |
| 1.00 | 1.0000 | 0.74 | 0.615 | 1.7921 |
| 1.50 | 0.6667 | 0.64 | 0.792 | 1.3605 |
| 2.00 | 0.5000 | 0.52 | 1.260 | 0.8313 |

Note that in Table 3, 0.057 ppb is subtracted to correct the fluorescence.

As shown in Table 4, non-weighted regression analysis of Stem-Volmer plots for the above data have 'goodness-of-fit' ($r^2$) of approximately 90% for the field data and 99% for the laboratory data. Data using the Hitachi research grade Fluorometer presumably has a higher fit due to more accurate fluorescence measurements with significantly lower background light being detected.

TABLE 4

| | Example #1 | Example #2 | Example #3 |
|---|---|---|---|
| $r^2$ | 99% | 89% | 89% |
| $K_d[Q]$ | 91.5 | 642.4 | 141.3 |

These data suggest that the quenching rate constant multiplied by the quencher concentration varies with the water being treated. This variability with respect to the water tested suggests that quenching may be related to water treatability such that quenching can be advantageously used as a water treatment parameter.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:
1. A method of monitoring residual treating agent in water treatment process water comprising
   i) adding a first dose of a treating agent traced with a fluorescent tracer to a first sample of the process water,
   ii) measuring the fluorescence response of the first sample of the process water,
   iii) adding a second, different dose of the treating agent traced with the fluorescent tracer to a second sample of the process water; and
   iv) measuring the fluorescence response of the second sample of the process water, wherein the residual concentration of the treating agent is estimated using the change in measured concentration of the fluorescent tracer at the respective treating agent doses using a function of the difference between the fluorescence quenching expected and the fluorescence quenching detected.
2. The method of claim 1 wherein the residual concentration of the treating agent is correlated with treating agent dosage.
3. The method of claim 1 wherein the residual concentration of the treating agent is used to determine an upper and lower limit of treating dosage.
4. The method of claim 3 wherein the treating agent dosage is automatically maintained between the upper and lower limit.
5. The method of claim 1 wherein the water treatment process is a solid-liquid separation process.

6. The method of claim 5 wherein the solid-liquid separation process comprises treatment of the water with one or more coagulants or flocculants, or a combination thereof, to form a mixture of water and coagulated and flocculated solids and separation of the coagulated and flocculated solids from the water.

7. The method of claim 6 wherein the solid-liquid separation process is a membrane separation process wherein the coagulated and flocculated solids are separated from the water by filtration through a membrane.

8. The method of claim 7 further comprising one or more pretreatment steps wherein a portion of the coagulated and flocculated solids are separated from the water prior to filtration of the water through the membrane.

9. A method of monitoring filter aid residuals in treated water in a reverse osmosis pretreatment program wherein the water is treated with one or more filter aids to form a mixture of coagulated and flocculated solids and at least a portion of the coagulated and flocculated solids are removed from the water prior to filtration through a reverse osmosis membrane comprising
   i) adding a first dose of a filter aid traced with a fluorescent tracer to a first sample of the water to form a mixture comprising water, coagulated and flocculated solids and filter aid traced with a fluorescent tracer;
   ii) separating at least a portion of the coagulated and flocculated solids from the first sample of the water;
   iii) measuring the fluorescence response of the first sample of the water;
   iv) adding a second, different dose of the filter aid traced with the fluorescent tracer to a second sample of the water to form a second mixture comprising water, coagulated and flocculated solids and filter aid traced with a fluorescent tracer;
   v) separating at least a portion of the coagulated and flocculated solids from the second sample of the water;
   vi) measuring the fluorescence response of the second sample of the water; and
   vii) using the fluorescence response at the respective filter aid dosages to estimate the residual concentration of the filter aid.

10. The method of claim 9 wherein the residual concentration of the filter aid is estimated using the change in measured concentration of the fluorescent tracer at the respective filter aid doses using a function of the difference between molecules of fluorescent tracer added to the water and molecules of fluorescent tracer detected in the water.

11. The method of claim 9 wherein the residual concentration of the filter aid is estimated using the change in measured concentration of the fluorescent tracer at the respective filter aid doses using a function of the difference between the fluorescence quenching expected and the fluorescence quenching detected.

12. The method of claim 9 wherein the residual concentration of the filter aid is correlated with treating agent dosage.

13. The method of claim 9 wherein the residual concentration of the filter aid is used to determine an upper and lower limit of treating dosage.

14. The method of claim 13 wherein the filter aid dosage is automatically maintained between the upper and lower limit.

15. The method of claim 9 wherein the portion of coagulated and flocculated solids is removed from the water by filtration through a media filter.

16. The method of claim 9 wherein the filter aid is one or more coagulants selected from alum, polyaluminum chloride, ferric chloride, ferric sulfate, poly(diallyldimethylammonium chloride) and Epi-DMA.

17. The method of claim 9 wherein the fluorescent tracer is selected from fluorescein, rhodamine B, and rhodamine WT.

18. A method of monitoring residual treating agent in solid-liquid separation process water comprising
   i) adding a first dose of a treating agent traced with a fluorescent tracer to a first sample of the process water,
   ii) measuring the fluorescence response of the first sample of the process water,
   iii) adding a second, different dose of the treating agent traced with the fluorescent tracer to a second sample of the process water;
   iv) measuring the fluorescence response of the second sample of the process water; and
   v) using the fluorescence response at the respective treating agent dosages to estimate the residual concentration of the treating agent.

19. The method of claim 18 wherein the residual concentration of the treating agent is estimated using the change in measured concentration of the fluorescent tracer at the respective treating agent doses using a function of the difference between molecules of fluorescent tracer added to the water and molecules of fluorescent tracer detected in the water.

20. The method of claim 18 wherein the residual concentration of the treating agent is estimated using the change in measured concentration of the fluorescent tracer at the respective treating agent doses using a function of the difference between the fluorescence quenching expected and the fluorescence quenching detected.

21. The method of claim 18 wherein the residual concentration of the treating agent is correlated with treating agent dosage.

22. The method of claim 18 wherein the residual concentration of the treating agent is used to determine an upper and lower limit of treating dosage.

23. The method of claim 22 wherein the treating agent dosage is automatically maintained between the upper and lower limit.

* * * * *